(12) United States Patent
 Culberson

(10) Patent No.: US 8,998,157 B2
(45) Date of Patent: Apr. 7, 2015

(54) MOLAR MEDIA MOUNT

(71) Applicant: Casey F Culberson, Mill Creek, WA (US)

(72) Inventor: Casey F Culberson, Mill Creek, WA (US)

( * ) Notice: Subject to any disclaimer, the term of this patent is extended or adjusted under 35 U.S.C. 154(b) by 0 days.

(21) Appl. No.: 13/961,800

(22) Filed: Aug. 7, 2013

(65) Prior Publication Data

US 2014/0045139 A1  Feb. 13, 2014

Related U.S. Application Data

(60) Provisional application No. 61/682,013, filed on Aug. 10, 2012.

(51) Int. Cl.
| *A47H 1/10* | (2006.01) |
| *H05K 5/00* | (2006.01) |
| *H05K 5/02* | (2006.01) |
| *A61C 1/08* | (2006.01) |
| *A61G 15/14* | (2006.01) |
| *F16M 11/14* | (2006.01) |
| *F16M 11/20* | (2006.01) |
| *F16M 13/02* | (2006.01) |

(52) U.S. Cl.
CPC ............ *H05K 5/0017* (2013.01); *H05K 5/0217* (2013.01); *A61C 1/088* (2013.01); *A61G 15/14* (2013.01); *F16M 11/14* (2013.01); *F16M 11/2021* (2013.01); *F16M 13/02* (2013.01); *F16M 2200/022* (2013.01); *Y10S 248/921* (2013.01)

(58) Field of Classification Search
CPC ... H05K 5/0017; H05K 5/0217; A61C 1/088; A61G 15/14; F16M 11/14; F16M 11/2021; F16M 13/02; F16M 220/022
USPC ................. 248/205.3, 231.61, 231.85, 284.1, 248/288.31, 316.6, 316.8, 317, 918, 921, 248/922, 323, 324, 316.1; 362/287, 147, 362/232
See application file for complete search history.

(56) References Cited

U.S. PATENT DOCUMENTS

| 2,563,473 | A | * | 8/1951 | Levinson | 433/29 |
| 4,170,336 | A | * | 10/1979 | Malis | 248/279.1 |
| 4,562,987 | A | * | 1/1986 | Leeds et al. | 248/278.1 |
| 5,154,390 | A | * | 10/1992 | Bain et al. | 248/447.2 |
| 6,086,228 | A | * | 7/2000 | McGowan et al. | 362/396 |
| 6,220,556 | B1 | * | 4/2001 | Sohrt et al. | 248/279.1 |
| 6,839,978 | B2 | * | 1/2005 | Allen | 33/642 |
| 2003/0071184 | A1 | * | 4/2003 | Parkinson | 248/346.01 |

* cited by examiner

*Primary Examiner* — Gwendolyn Baxter
(74) *Attorney, Agent, or Firm* — Plager Schack LLP

(57) ABSTRACT

Some embodiments provide a molar media mount for positioning a media display device in unobscured view and direct line of sight of a patient. In some embodiments, the molar media mount includes a first end that attaches to a mounting arm of a medical device and a second end that attaches to and holds the media display device. In some embodiments, the second end includes a ball joint for setting an angle of the media display device that corresponds to the direct line of sight. In some embodiments, the molar media mount includes a set of articulating points that position a media display screen in a direct line of sight of a person in an examination seat In some embodiments, the medical device is a dental light. In some embodiments, the media display device attaches to the dental light.

9 Claims, 4 Drawing Sheets

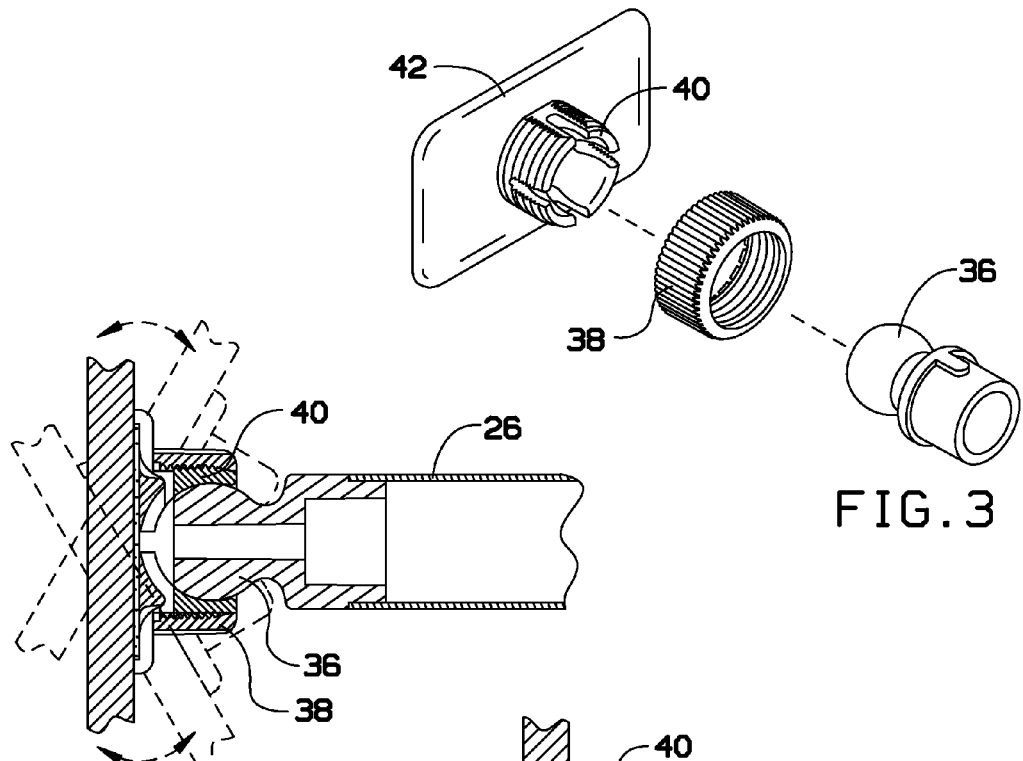
FIG. 3
FIG. 4
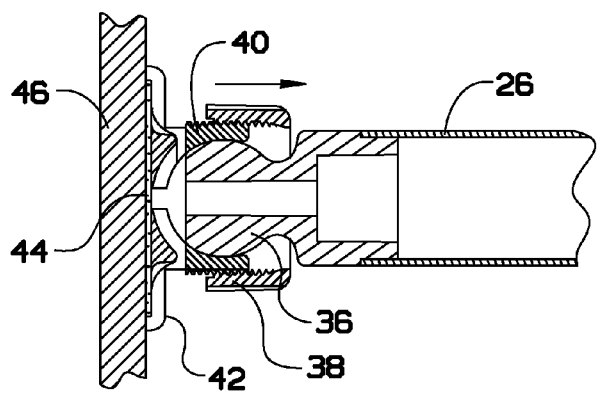
FIG. 5
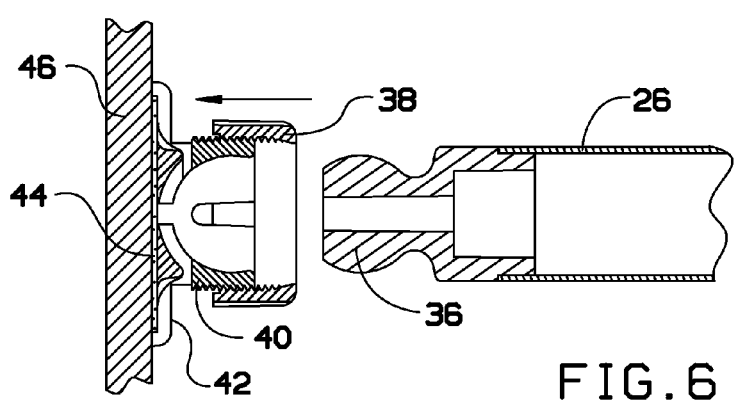
FIG. 6

MOLAR MEDIA MOUNT

CLAIM OF BENEFIT TO PRIOR APPLICATION

This application claims benefit to U.S. Provisional Patent Application 61/682,013, entitled "An arm that attaches to dental light and holds a media device for patient viewing," filed Aug. 10, 2012. The U.S. Provisional Patent Application 61/682,013 is incorporated herein by reference.

BACKGROUND

The embodiments herein relate generally to media device mounts, and more particularly to media device mounts for patient viewing in dental offices.

Media devices are often provided in medical offices and exam rooms to display media content for patients to view during an examination or a procedure. For instance, a video display device may be available in a dental office to allow dental patients to watch an entertaining video during a dental procedure. A variety of content can be displayed on these display devices for a variety of needs. For example, display devices may be used to display images or video of a patient's tissue or body part(s) related to a procedure, to instruct the patient on preventive or post-procedure care, or to simply engage a patient in something that preoccupies them so as to calm their nerves during a procedure. In particular, in dental offices, the types of content may include, for example, entertaining videos, dental imagery of the patient (e.g., a color picture of the patient's gum line, an x-ray image of a cavity on one of the patient's teeth, etc.), educational videos (e.g. instructional videos that children may watch to learn proper brushing techniques, etc.), and many other types of content.

Such media devices are typically mounted on the ceiling or mounted to an arm that hangs from the ceiling. From the perspective of the patient, the mounting or hanging position of the display device must be capable of providing a view angle to the display that is generally unobscured and is preferably defined along a direct line of sight from the patient's eyes. However, most medical and dental procedures require movements of one or more medical personnel (e.g., dentists, doctors, specialists, assistants, etc.) during the procedure. Movements, such as arm and head movements of positioned medical personnel and full body relocations of personnel, often break the viewing angle between the patient and the media display device. This is problematic for patients and medical practitioners who wish to maintain a generally direct line of sight between the patient and a media display device in an examination room.

Additionally, most displays mounted to arms require a set of wires to provide content data to display the video(s) and/or image(s), electrical current to power the display, communication and command data to control playback of the content and/or view settings of the display (e.g., contrast ratio, color depth, etc.). As a result, current media arms are large and bulky, are only mountable to positions that severely limit the range of movement from which the display can be positioned, and are limited in the viewing angle at which the patient can view the display.

Thus, what is needed is a small, lightweight arm that attaches to an existing arm configured to provide operation of a medical device (e.g., a dental light above a patient that provides light for the dentist to perform dental procedures), such that the arm can hold a media device next to the light itself in a proper viewing distance for the patient to view content and at a direct line of sight viewing angle for the patient.

BRIEF SUMMARY

Some embodiments of the invention provide a molar media mount for positioning a media display device in a direct line of sight of a patient. In some embodiments, the molar media mount comprises a first end that attaches to a mounting arm of a medical device and a second end that attaches to and holds the media display device. In some embodiments, the second end comprises a ball joint for setting an angle of the media display device that corresponds to the direct line of sight. In some embodiments, the molar media mount comprises a set of articulating points that position a media display screen in a direct line of sight of a person in an examination seat In some embodiments, the medical device is a dental light. In some embodiments, the media display device attaches to the dental light.

BRIEF DESCRIPTION OF THE DRAWINGS

Having described the invention in general terms, reference is now made to the accompanying drawings, which are not necessarily drawn to scale, and wherein:

FIG. 3 conceptually illustrates a detail rear exploded view of a ball joint in some embodiments of a molar media mount.

FIG. 4 conceptually illustrates a section view, along line 4-4 in FIG. 1, of a molar media mount in some embodiments, showing an example of movement of the mounting plate.

FIG. 5 conceptually illustrates a section view of a retaining nut for loosening a molar media mount in some embodiments.

FIG. 6 conceptually illustrates an example of removing the mounting plate in some embodiments.

DETAILED DESCRIPTION

In the following detailed description, several examples and embodiments of the invention are described. However, it will be clear to a person skilled in the art that the invention is not limited to the embodiments set forth and can be adapted for any of several other uses in which a line of sight to an item is required.

Some embodiments of the invention provide a molar media mount for positioning a media display device in a direct line of sight of a patient. In some embodiments, the molar media mount comprises a first end that attaches to a mounting arm of a medical device and a second end that attaches to and holds the media display device. In some embodiments, the second end comprises a ball joint for setting an angle of the media display device that corresponds to the direct line of sight. In some embodiments, the molar media mount comprises a set of articulating points that position a media display screen in a direct line of sight of a person in an examination seat In some embodiments, the medical device is a dental light. In some embodiments, the media display device attaches to the dental light.

Figure 1:
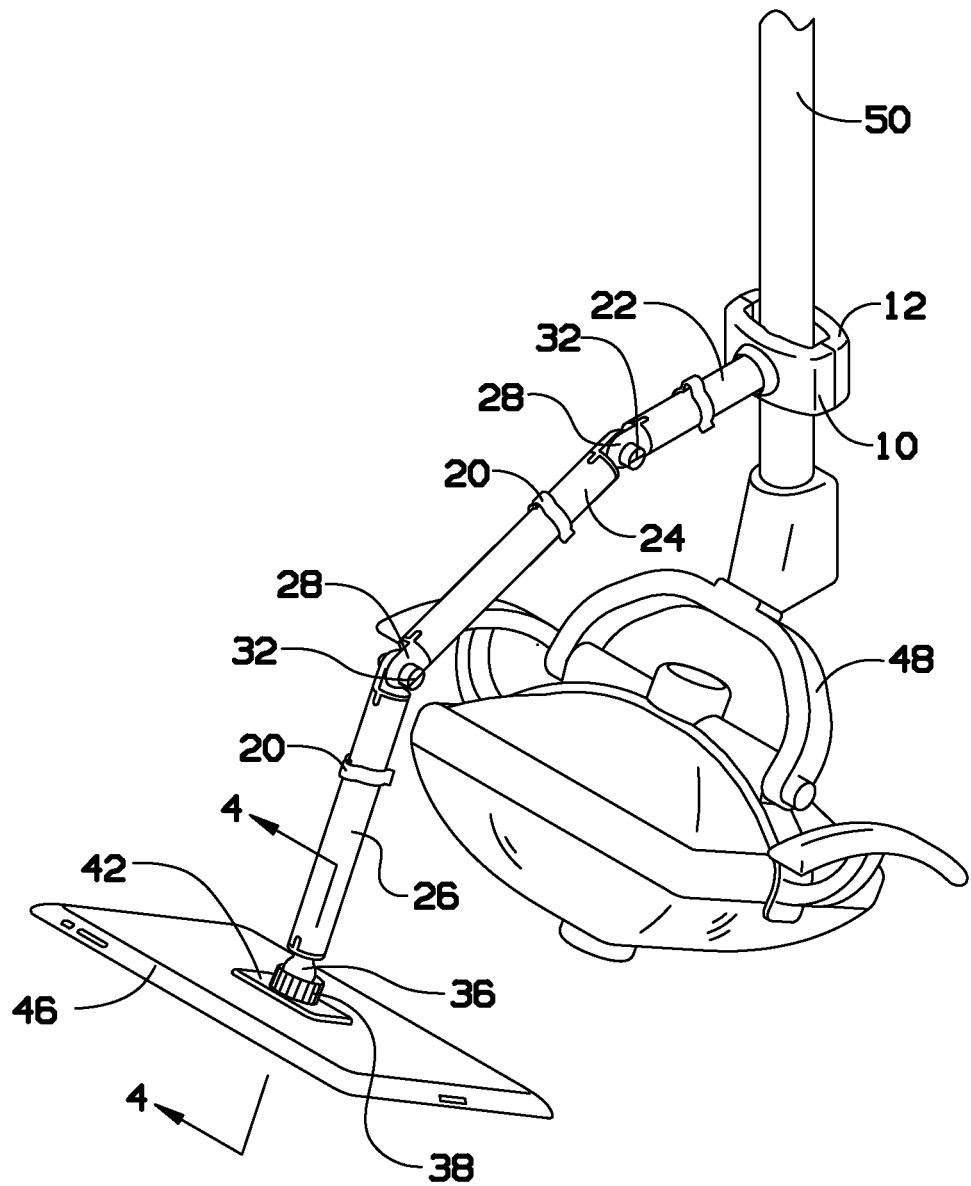
FIG. 1 conceptually illustrates a perspective view of a molar media mount in some embodiments.

FIG. 1 conceptually illustrates a perspective view of a molar media mount in some embodiments. In this figure, a media display device 46 is connected to the molar media mount for viewing of media content by a patient. As shown, the molar media mount comprises a front section of the mounting bracket 10, a rear section of the mounting bracket 12, a set of cable guide clips 20, a rear arm section 22, a middle arm section 24, a front arm section 26, a male pivot joint 28, a set of pivot joint thumb screws 32, a male ball joint 36, a ball joint retaining screw 38, and a mounting plate 42. In some embodiments, the rear arm section 22 is attached to the front mounting bracket section 10, which is attached together with the rear mounting bracket 12 around a mounting surface 50 to which a dental lamp 48 is attached.

In operation, the molar media mount acts as a media arm to hold a media display device that is viewable by a patient. In particular, the media arm attaches to the mounting surface of the dental lamp. Unlike the mounting surface of the dental lamp, however, the media arm shown in this example does not attach to the ceiling. This attachment to the mounting surface, and not the ceiling, allows the display device to be easily moved and re-angled as necessary to place the media display device directly in the patient's line of sight. Additionally, the direct line of sight is not broken even if the patient moves in the seat or if the clinician happens to move them or adjusts the lamp.

The molar media mount is positioned relative to the dental lamp 48 in some embodiments in order to provide direct viewing of content on the media display device 46. Specifically, the display device 46 maintains a direct line of sight to the patient because it is attached at the end of the molar media mount at a view angle that correlates to a shine angle of the dental lamp, which shines a source of light on the patient's mouth in order to allow a dentist to perform dental work.

Figure 2:
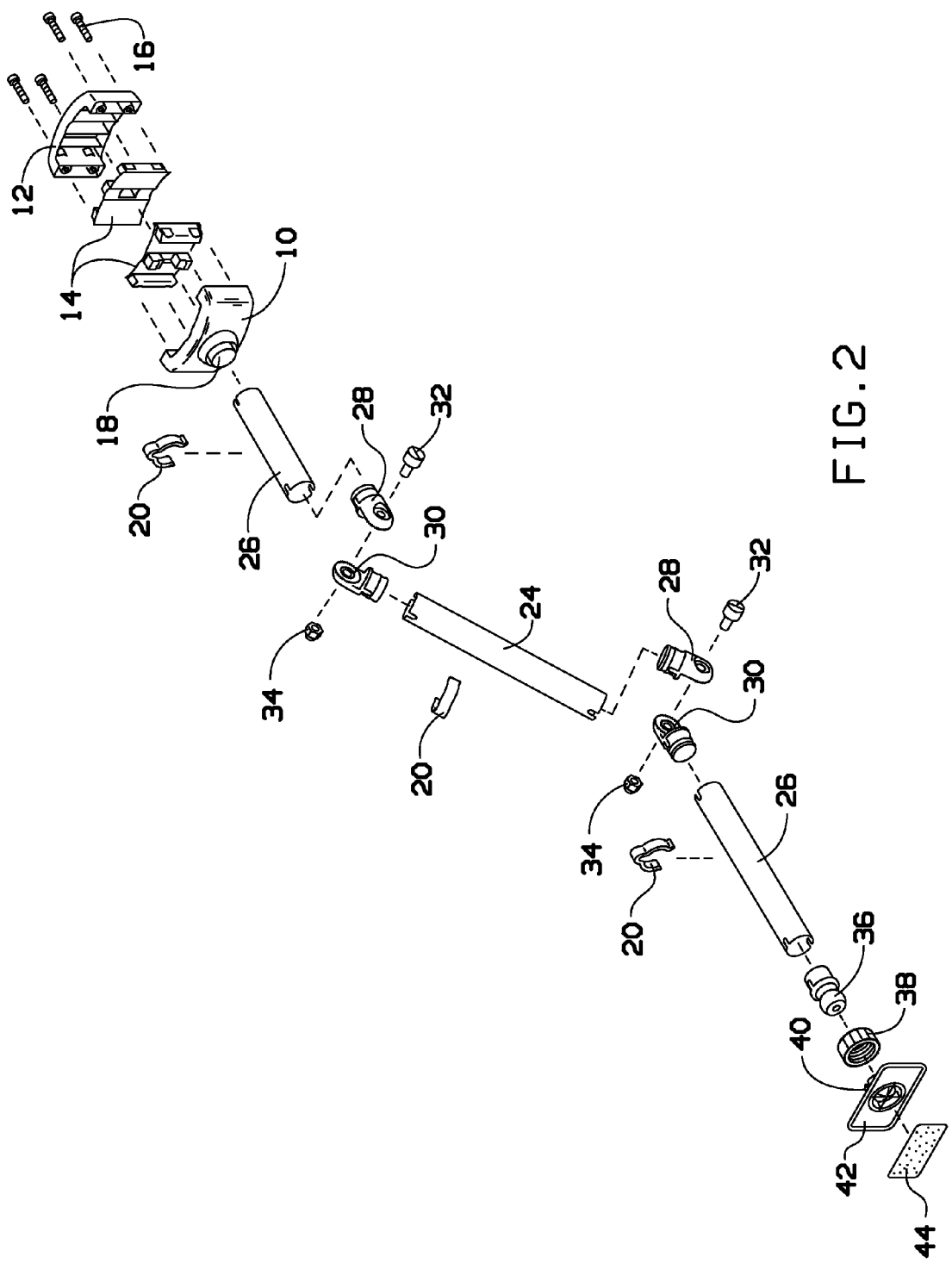
FIG. 2 conceptually illustrates an exploded view of a molar media mount in some embodiments.

FIG. 2 conceptually illustrates an exploded view of a molar media mount in some embodiments. The molar media mount shown in this figure is similar to the molar media mount illustrated in FIG. 1, except that several additional items are shown in this view. As shown, the additional items of the molar media mount comprise a set of bracket inserts 14, a set of machine screws 16, a front brake arm connection point 18, a set of female pivot joints 30, a set of pivot joint nuts 34, a ball joint cup 40, and an adhesive 44. In some embodiments, media display device is attached to the media arm by a ball joint assembly comprising the adhesive 44 that attaches to the mounting plate 42, which is thereby connected to a ball cup joint 36.

The ball joint assembly is further described by reference to FIG. 3, which conceptually illustrates a detail rear exploded view of a ball joint in some embodiments of a molar media mount. Specifically, the mounting plate 42 attaches to a female end of a ball cup joint 40, which is secured to the male end of the ball cup joint 40 by the ball joint retaining screw 38. A male ball joint 36 is attached to the other end of the ball joint retaining screw 38.

Referring back to FIG. 2, the male ball joint 36 connects at the other end to the front arm section 26. On top of the front arm section 26 is at least one cable guide clip 20. The front arm section 26, in combination with the ball joint assembly described above, and the media display device, forms a functional assembly of the media mount along line 4-4 of FIG. 1. Specifically, this functional assembly is described by reference to FIGS. 4-6.

FIG. 4 conceptually illustrates a section view, along line 4-4 in FIG. 1, of a molar media mount in some embodiments, showing an example of movement of the mounting plate. As shown, the ball joint retaining screw 38 screws over the ball cup joint 40 where the male ball joint 36 fits. Specifically, this example shows movement (i.e., shown by the arrows) of the media display device in each of several different manners. Although shown in several conceptual example positions, the media display device can be positioned at any position along a range of positions. By securing the media display device in this manner, a user (e.g., a dentist) can use the device to provide entertainment to a patient during a dental exam or procedure. The design is efficient and cost effective, thus providing affordable entertainment that can be adjusted in an effective way so as not to disrupt the dental procedure while maintaining direct line of sight with the patient.

FIG. 5 conceptually illustrates a section view of a retaining nut for loosening a molar media mount in some embodiments. In this example, a dentist or other use can remove any type of display from the media arm by loosening the retaining screw 38 (shown by arrow). Because the male ball joint 36 fits in the ball cup joint, any display that is attached is secured to the media arm for movement to any of several viewing angles (i.e., as described by reference to FIG. 4). Yes, when the retaining screw 38 is loosened, the ball joint 38 is easily removed. Likewise, attaching a display can be performed with relative ease by a dentist or other authorized person. This is shown by the arrow in FIG. 6, which conceptually illustrates an example of removing the mounting plate in some embodiments. Specifically, the male ball joint is aligned with the ball cup joint 40. When put into the ball cup joint 40, the retaining screw 38 can be tightened (as shown by the arrow) in order to secure the connection.

Many of the examples above described assembly of the media arm in some embodiments, and function of individual components or sub-assemblies. In the next examples, the function of the overall media arm and media mount is described. These examples are described by reference to FIG. 7, which illustrates a full range of motion of a molar media mount in some embodiments, and FIG. 8, which shows an alternate embodiment in which the media arm is mounted directly to the dental lamp, instead of the mounting surface.

Figure 7:
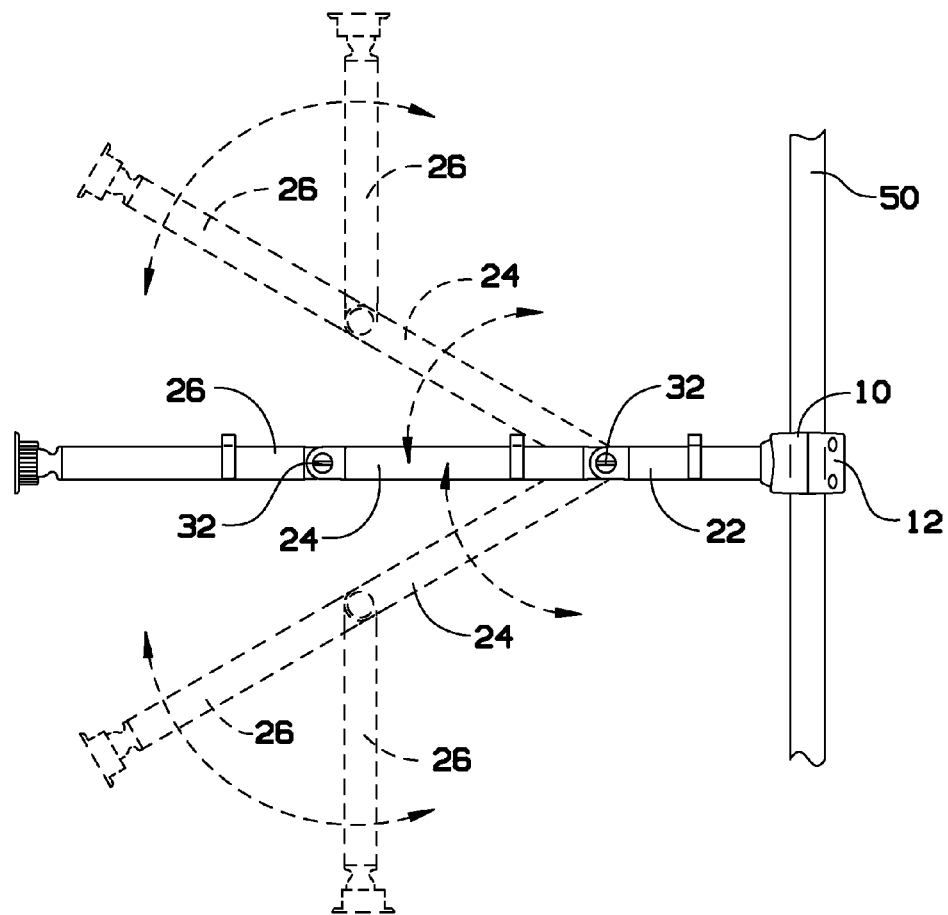
FIG. 7 conceptually illustrates an example of moving a set of pivoting arms of a molar media mount in some embodiments.

FIG. 7 conceptually illustrates an example of moving a set of pivoting arms of a molar media mount in some embodiments. As shown, each elongated section 26, 24, and 22, can be positioned in line with the other elongated sections or at an offset angle from one or both of the other elongated sections. Since the elongated sections 26, 24, and 22 are connected by pivot joint thumb screws 32, a full range of motion is permitted for each offset angle at which an elongated section may be positioned. In this way, the media display device can be configured for viewing at any angle with respect to the patient.

In addition, the media arm is mounted in this example to the mounting surface of an existing hanging mount arm. In some cases, the mounting surface is a legacy mounting arm of a dental lamp, and thus, is available for attaching the molar media arm of some embodiments. Moreover, if mounted to an existing installation (such as mounting surface 50), the molar media mount arm can be adjusted vertically along the mounting surface. This is accomplished by loosening the brackets 10 and 12 that surround the mounting surface 50 and moving the media arm up and/or down as needed. For instance, the media arm can be adjusted up for cleaning or for other purposes.

Figure 8:
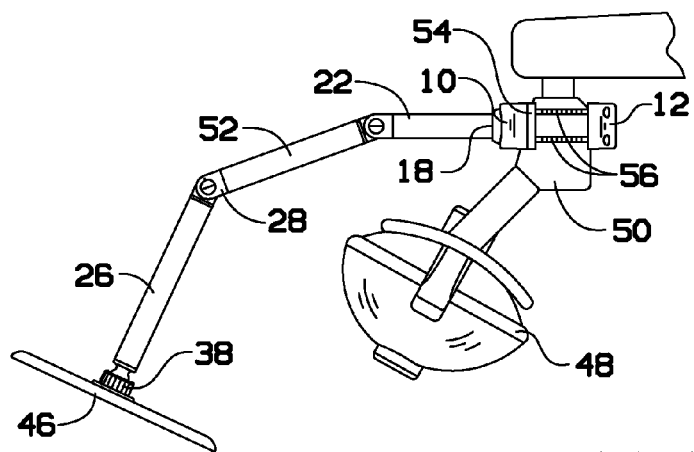
FIG. 8 conceptually illustrates a side view of an alternative molar media mount in some embodiments.

FIG. 8 conceptually illustrates a side view of an alternative molar media mount in some embodiments. As shown in this example, the molar media mount is attached directly to the dental lamp, not to an existing installation, such as the mounting surface 50. Specifically, the mounting surface 50 in this case is the dental lamp. Also, the media arm of this example includes a alternate middle arm section 52, an alternate wedge insert 54, and alternate machine screws 56. Thus, as can be seen in this figure, there are different options for mounting a media arm to provide a media display device that maintains a direct line of sight with the patient during a medical or dental examination or procedure.

Also, although the invention is illustrated with two mounting options, it should be noted that various inserts and machine screw lengths will allow the bracket to attach to a variety of surfaces, and such modifications in component configuration may be made without departing from the spirit and scope of the invention.

The above-described embodiments of the invention are presented for purposes of illustration and not of limitation.

I claim:

1. A media arm that holds a media display device in unobscured view and direct line of sight of a patient during a medical procedure, the media arm comprising:
    a plurality of elongated arm sections;
    a plurality of pivot joint thumb screws, each thumb screw connecting two elongated arm sections for angled offset positioning;
    a first attachment assembly connected to the end of an outermost elongated arm section, the first attachment assembly for connecting a media display device that displays one or more of entertainment videos, images of procedure-related items, and educational video content; and
    a second attachment assembly connected an inner-most elongated arm section, the second attachment assembly for connecting to a mounting surface, wherein the mounting surface is an existing dental lamp mount connected to the ceiling of an examination room, wherein the second attachment assembly comprises a pair of brackets that attach to each other around the mounting surface to secure the media arm to the mounting surface.

2. The media arm of claim 1, wherein the media display device is configured to maintain a direct line of sight to the patient during any repositioning of the device.

3. The media arm of claim 1, wherein the plurality of elongated arm sections comprises an outer arm section, a middle arm section, and an inner arm section.

4. The media arm of claim 3, wherein the outer arm section comprises the outermost elongated arm section, wherein the inner arm section comprises the inner-most elongated arm section.

5. The media arm of claim 1, wherein each of the elongated sections is movable along a range of offset angles defined by a joint that connects the elongated section to another elongated section.

6. The media arm of claim 5, wherein the range of offset angles comprises all angles in 360 degrees.

7. The media arm of claim 5, wherein the range of offset angles comprises all angles in a defined range of angles less than 360 degrees.

8. A media arm that holds a media display device in unobscured view and direct line of sight of a patient during a medical procedure, the media arm comprising:
    a plurality of elongated arm sections;
    a plurality of pivot joint thumb screws, each thumb screw connecting two elongated arm sections for angled offset positioning;
    a first attachment assembly connected to the end of an outermost elongated arm section, the first attachment assembly comprising a mounting plate, a ball joint, a retaining screw, and an adhesive, wherein the first attachment assembly is for connecting the media display device; and
    a second attachment assembly connected an inner-most elongated arm section, the second attachment assembly for connecting to a mounting surface, wherein the mounting surface is an existing dental lamp mount connected to the ceiling of an examination room, wherein the second attachment assembly comprises a pair of brackets that attach to each other around the mounting surface to secure the media arm to the mounting surface.

9. The media arm of claim 8, wherein the adhesive attaches a display device to the mounting plate and the retaining screw secures a connection between a ball connector of the media arm that fits in the ball joint.

* * * * *